United States Patent [19]

Kido et al.

[11] Patent Number: 4,801,434

[45] Date of Patent: Jan. 31, 1989

[54] DUAL PIPETTE DEVICE

[75] Inventors: Keishiro Kido; Yoshio Saito, both of Saitama; Takashi Koizumi, Kanagawa; Osamu Seshimoto, Saitama, all of Japan

[73] Assignee: Fuji Photo Film Co., Ltd., Kanagawa, Japan

[21] Appl. No.: 938,192

[22] Filed: Dec. 5, 1986

[30] Foreign Application Priority Data

Dec. 6, 1985 [JP] Japan .................................. 60-274710
Dec. 12, 1985 [JP] Japan .................................. 60-279840
Jan. 28, 1986 [JP] Japan .................................. 61-16077

[51] Int. Cl.$^4$ .............................................. B01L 3/02
[52] U.S. Cl. .................... 422/100; 73/863.32; 73/864.13; 73/864.14; 73/864.17; 73/864.87
[58] Field of Search ............... 422/100, 64, 63; 73/864.01, 864.25, 863.31, 863.32, 863.33, 863.82, 863.83, 863.84, 864.13, 864.14, 864.16, 864.17, 864.18, 864.87; 604/191; 141/27, 258, 242, 243

[56] References Cited

U.S. PATENT DOCUMENTS

| 3,853,008 | 12/1974 | Hoffa et al. ......................... 422/63 |
| 3,855,868 | 12/1974 | Suduaniemi ....................... 73/863.32 |
| 4,009,611 | 3/1977 | Koffer et al. ...................... 73/864.14 |
| 4,260,077 | 4/1981 | Schroeder ............................ 604/191 |

FOREIGN PATENT DOCUMENTS 60-13260  1/1985  Japan .
6504453 10/1966 Netherlands ..................... 73/863.32

Primary Examiner—Benoit Castel
Attorney, Agent, or Firm—Sughrue, Mion, Zinn, Macpeak & Seas

[57] ABSTRACT

A dual pipette device comprises a pair of housings joined rotatably around a vertically extending axis or disposed for lateral movement, a pair of cylinders disposed respectively at lower sections of the housings, a pair of piston members extending vertically, supported by the housings or the cylinders, and respectively having lower end portions vertically slideable in the cylinders, and dropping tip fitting sections disposed at lower end of the housings or the cylinders so that the dropping tip fitting sections communicate with the cylinders. The piston members are provided with a lock member for locking them to each other when the housings are rotated or laterally moved and the distance between the piston members becomes not larger than a predetermined distance, so that the piston members are vertically slideable integrally with each other.

18 Claims, 7 Drawing Sheets

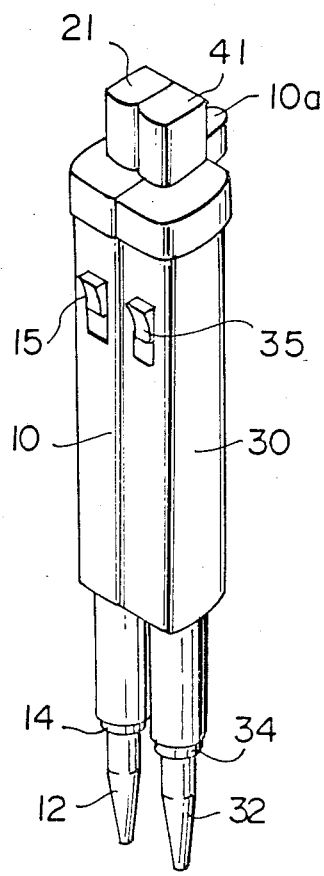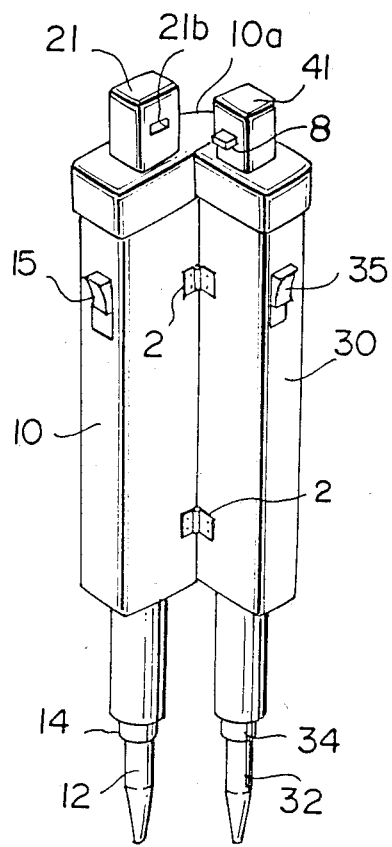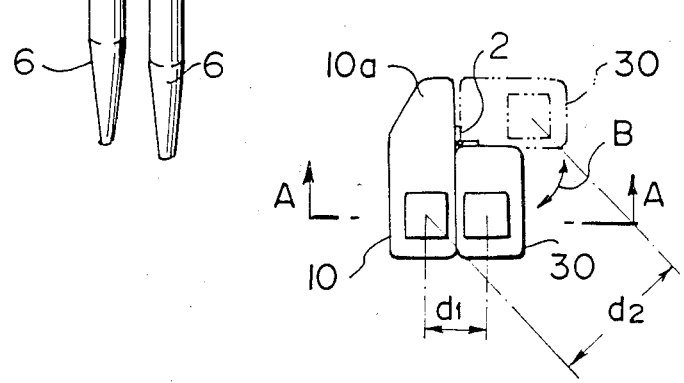

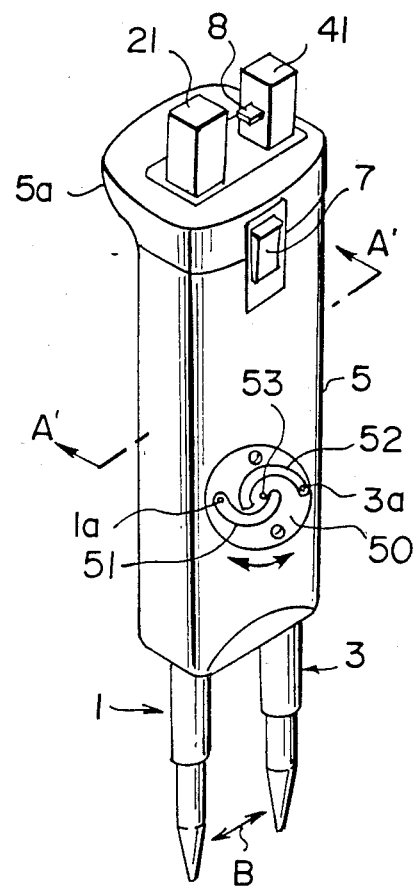
FIG.5
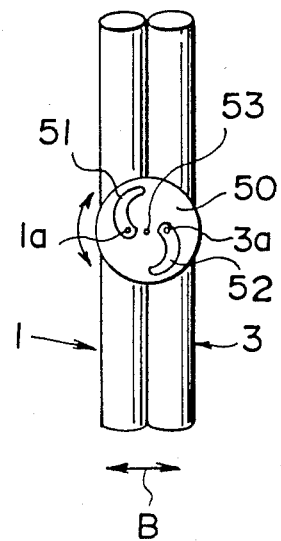
FIG.7
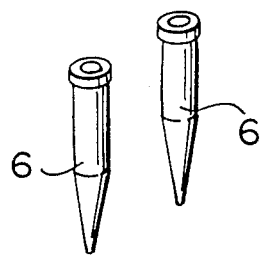

FIG.11
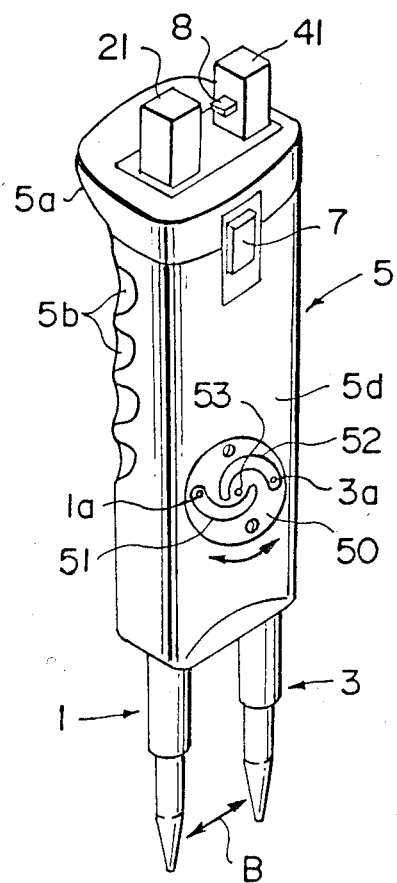
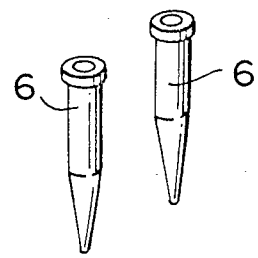

DUAL PIPETTE DEVICE

BACKGROUND OF THE INVENTION

1. Field of the Invention

This invention relates to a dual pipette device for drawing two different liquids thereinto by suction and ejecting the liquids therefrom. This invention particularly relates to a dual pipette device suitable for feeding a sample solution and a reference solution by spotting to a slide type ionic activity measuring device.

2. Description of the Prior Art

As disclosed in, for example, Japanese unexamined patent publication Nos. 58(1983)-211648 and 59(1984)-30055 and Japanese patent application No. 59(1984)-11744, there has been proposed an ionic activity measuring device for receiving an aqueous liquid sample, for example, a wine, a beverage, service water, particularly a body fluid (blood, urine, saliva or the like), which is fed by spotting, and quantitatively analyzing the activity or concentration of a predetermined ion contained in the sample by potentiometry.

In general, the ionic activity measuring device is provided with at least one set of ion selective electrode pairs having an ion selective layer selectively responding to a predetermined ion as the outermost layer. In the disclosures referred to above, the ion selective electrode pair is supported between an upper frame and a lower supporting frame. The upper frame is provided with a pair of liquid access holes positioned to correspond to the set of the ion selective electrode pair. A porous bridge (preferably constituted by twisted fiber yarn) is disposed, usually on the upper frame, for achieving electrical conduction through liquid junction between sample liquid fed to one of the pair of the liquid access holes and reference solution fed to the other. In the case where multiple sets of the ion selective electrode pairs are provided, a pair of porous liquid distributing members are disposed generally between the upper frame and the ion selective electrode pairs for communicating the ion selective electrode pairs with the pair of liquid access holes.

In the case where the ionic activity measuring device having the aforesaid configuration is provided with, for example, three sets of the ion selective electrode pairs responding respectively to $Na^+$, $K^+$, and $Cl^-$ ions, a reference solution having known activity values of these ions is spotted to one of the pair of the liquid spotting holes, and a sample solution wherein the activity values of these ions are unknown is spotted to the other of the pair of the liquid spotting holes. (The reference solution and the sample solution should preferably be spotted substantially at the same time.) The reference solution and the sample solution penetrate through the porous liquid distributing members to the corresponding ion selective electrodes. The sample solution and the reference solution penetrate to the porous bridge and join near the middle of the porous bridge to achieve liquid junction, and thus electrical conduction is accomplished between the two solutions. As a result, a potential difference arises between the electrodes of each ion selective electrode pair, being proportional to the difference in activity of each ion between the sample solution and the reference solution.

By measurement of the potential difference, it is possible to determine the activity of $Na^+$, $K^+$ and $Cl^-$ ions in the sample either simultaneously or separately, based on the calibration curves determined in advance using standard solutions having various activity values of ions (according to Nernst Equation).

With the aforesaid ionic activity measuring device, it is possible to measure the ionic activity simply by spotting the sample solution and the reference solution only once. Therefore, the ionic activity measuring device is very advantageous for analysis of an aqueous liquid sample, particularly for clinical analysis of a body fluid such as blood.

Preferably, the sample solution and the reference solution are fed to the ionic activity measuring device substantially at the same time. Therefore, a need exists for a spotting feed means suitable for the spotting operation. The use of a dual pipette device adapted to drawing-in and ejection of the sample solution and the reference solution with a single device would be particularly convenient as the liquid feeding means for the simple measurement of ionic activity.

The dual pipette device should preferably be constituted so that it has a pair of liquid dispensing tips from which the sample solution and the reference solution are dispensed simultaneously to the pair of the liquid access holes of the ionic activity measuring device. Specifically, the distance between dispensing tips of the dual pipette device should preferably be approximately equal to the distance between the liquid access holes of the ionic activity measuring device for feeding of the solutions to the device.

The distance between the liquid access holes of the ionic activity measuring device is usually very small (less than 1 cm). The distance between the pair of the liquid dispensing tips of the dual pipette device equal to the distance between the liquid access holes of the ion measuring device, which is so short, makes it difficult to draw a sample solution and a reference solution from a blood sampling tube, a reagent bottle or the like respectively into the dropping tips of the dual pipette device.

Particularly, for the measurement of ionic activity in a body fluid, it is desirable that the body fluid taken from the living body should be fed to the ionic activity measuring device so quickly that the body fluid may not be exposed to ambient atmosphere. It is preferred that the dual pipette device directly draw the sample solution from the living body or the like and simultaneously feed the sample solution and a reference solution, which is independently drawn into the dual pipette device to the pair of the liquid access holes of the ionic activity measuring device. However, no such dual pipette device has heretofore been known.

SUMMARY OF THE INVENTION

The primary object of the present invention is to provide a dual pipette device suitable for measurement of ionic activity conducted by using the aforesaid slide type ionic activity measuring device.

Another object of the present invention is to provide a dual pipette device suitable for feeding a sample solution and a reference solution correctly to corresponding liquid access holes of the aforesaid ionic activity measuring device having a pair or pairs of ion selective electordes.

The present invention provides a dual pipette device comprising:

(i) a pair of housings joined rotatably with respect to each other around a vertically extending axis, (ii) a pair of cylinders disposed respectively at lower sections of said housings, (iii) a pair of piston members extending vertically, supported by said housings or said cylinders, and respectively having lower end portions vertically slideable in said cylinders, and (iv) dropping tip fitting sections disposed at lower ends of said housings of said cylinders so that said dropping tip fitting sections communicate with said cylinders, wherein said pair of the piston members are provided with a lock mechanism for engaging said piston members with each other when said pair of the cylinders, thus the piston members, come close to each other within a predetermined distance by rotating the pair of housings around the vertical axis.

The present invention also provides a dual pipette device comprising a holding case, and a pair of pipettes disposed in parallel with each other and vertically extending in said holding case, wherein:

(i) said pair of the pipettes comprise a pair of cylinders, a pair of piston members extending vertically and respectively having lower end portions vertically slideable in said cylinders, and dropping tip fitting sections disposed at lower ends of said cylinders to communicate with said cylinders, (ii) said pair of the pipettes are disposed laterally moveably in said holding case so that the distance between said pipette is changeable, and (iii) said pair of the piston members are provided with a lock mechanism for engaging said piston members with each other when said pipettes are moved laterally with respect to each other and the distance between said pair of the piston members becomes not larger than a predetermined distance, so that said piston members are vertically slideable integrally with each other.

The present invention further provides a dual pipette device comprising a pair of pipettes disposed in parallel with each other, wherein outer surfaces of said dual pipette device grasped by a hand are formed so that one of two side surfaces positioned with said pair of the pipettes intervening therebetween has a shape adapted to grasping in a direction closely contacting said hand, and the other of said two side surfaces has a shape unadapted to grasping in the direction closely contacting said hand.

With the first and second mentioned dual pipette device in accordance with the present invention, by rotating the housings to the "open" position and thereby increasing the distance between cylinders, sample solution and reference solution can be drawn from a reagent bottle or the like more easily. Also, since the piston members are operable independently at the open position, it is possible to draw-in the sample solution and the reference solution independently with the respective piston members. When liquid is fed by spotting, the piston members are engaged with each other by rotating the housings or moving the pipettes to the "close" position so that the piston members can be operated integrally and the sample solution and the reference solution can be fed to the device simultaneously. When the distance between the dropping tips fitted to the lower ends of the housings or the pipettes is adjusted to be equal to the distance between a pair of the liquid spotting holes of the slide type ionic activity measuring device, it is possible to easily achieve the simultaneous spotting of the sample solution and the reference solution to the liquid spotting holes.

With the last mentioned dual pipette device in accordance with the present invention, wherein the outer surfaces of the holding case is provided with the finger gripping surface, the user always naturally grasps the dual pipette device in the same direction at the time of liquid drawing-in and spotting. Therefore, it is possible to feed the two different liquids correctly to corresponding liquid access holes of an ion activity measuring device without any special care and thus the efficiency of chemical analysis is improved markedly.

The dual pipette device in accordance with the present invention is suitable not only for measurement of ionic activity conducted by using the slide type ionic activity measuring device but also for spotting of a sample solution and a reference solution to other slide type dry colorimetric liquid analysis devices, colorimetric testpaper, colorimetric test pieces, or the like. This is very advantageous in practice.

By "dropping tips" are meant tip members provided with holes for dropping a sample solution and a reference solution in amounts (normally several tens of microliters) suitable for, for example, measurement of ionic activity conducted by using the slide type ionic activity measuring device. The dropping tips should preferably have a shape adapted to releasable fitting to the dropping tip fitting sections. Particularly, since the dropping tip for drawing and retaining the sample solution therein must be replaced by a clean dropping tip for each sample, the shape of the dropping tip for the sample solution should preferably be adapted to releasable fit to the dropping tip fitting section.

The means for operating the piston members may be automatic or manual, and any known vertical movement mechanism based on pneumatic pressures, hydraulic pressures, electromagnetic force (of solenoids, electrically operated motors, or the like), or the like may be used for this purpose.

BRIEF DESCRIPTION OF THE DRAWINGS

FIGS. 1 and 2 are perspective views showing an embodiment of the dual pipette device in accordance with the present invention, FIG. 3 is a plan view showing the embodiment of FIG. 1, FIG. 5 is a perspective view showing another embodiment of the dual pipette device in accordance with the present invention, FIG. 11 is a perspective view showing a further embodiment of the dual pipette device in accordance with the present invention.

DESCRIPTION OF THE PREFERRED EMBODIMENTS

Figure 4:
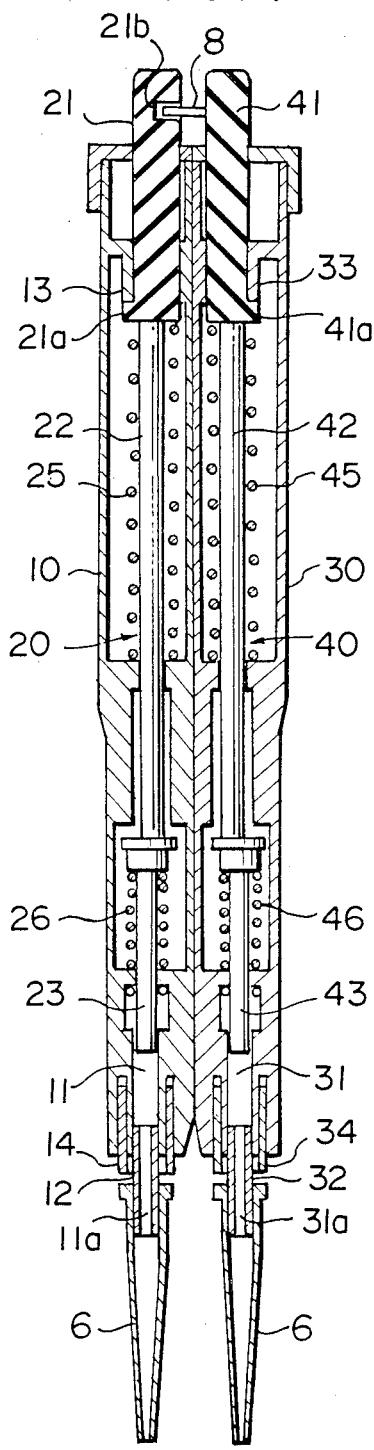
FIG. 4 is a sectional view taken along line A—A of FIG. 3.

The present invention will hereinbelow be described in further detail with reference to the accompanying drawings.

Referring to FIGS. 1 and 2, an embodiment of the dual pipette device in accordance with the present invention comprises a pair of housings 10 and 30, and a pair of piston members 20 and 40 disposed in the housings 10 and 30. As shown in FIG. 2, the housings 10 and 30 are joined together by hinges 2, for rotation around a vertically extending axis. Therefore, as indicated by the solid line and the chain line in FIG. 3, the second housing 30 is rotatable with respect to the first housing 10 by approximately 90° in the direction as indicated by the arrow B. This embodiment will further be described with reference to FIGS. 1, 2, 3 and 4.

The housings 10 and 30 joined by the hinges 2, are respectively provided with cylinders 11 and 31 at the lower sections. Also, dropping tip fitting sections 12 and 32 adapted to releasable fitting of dropping tips 6, 6 thereto and respectively having communication holes 11a and 31a communicating with the cylinders 11 and 31 are formed at the lower ends of the housings 10 and 30. A pair of vertically extending piston members 20 and 40 are disposed respectively in the housings 10 and 30. The piston members 20 and 40 respectively comprise push rods 21 and 41 disposed at the upper end sections and projecting upwardly from the upper surfaces of the housings 10 and 30, piston rods 23 and 43 disposed at the lower end sections and fitted to the cylinders 11 and 31 for vertical sliding therein, and connection rods 22 and 42 for connecting the push rods 21 and 41 with the piston rods 23 and 43. The piston members 20 and 40 are respectively urged upwardly with respect to the housings 10 and 30 by upper coil springs 25 and 45, and lower coil springs 26 and 46. The upward urging force of the upper coil springs 25 and 45, and the lower coil springs 26 and 46 are received by stop members 13 and 33 of the housings 10 and 30 which respectively contact step-like sections 21a and 41a of the push rods 21 and 41.

Tip ejectors 14 and 34 vertically moveable in the housings 10 and 30 are respectively disposed at the lower ends of the housings 10 and 30 so as to surround the dropping tip fitting sections 12 and 32. The tip ejectors 14 and 34 are respectively connected to ejector knobs 15 and 35 mounted on the outer side surfaces of the housings 10 and 30. When the ejector knobs 15 and 35 are operated downwardly, the tip ejectors 14 and 34 are pushed down to eject the dropping tips 6, from the dropping tip fitting sections 12 and 32. Therefore, it is possible to remove the used dropping tips from the dual pipette device without directly touching the dropping tips after spotting of the sample solution or the reference solution is finished.

Also, a lock groove 21b is formed in the inner side surface of the first push rod 21, and a lock member 8 is secured to the inner side surface of the second push rod 41. When the housings 10 and 30 are positioned so that the side surfaces thereof closely contact as shown in FIG. 1 (this position will hereinafter be referred to as the close contact position), the lock member 8 enters the lock groove 21b as shown in FIG. 4, thereby locking the push rods 21 and 41 to each other. Therefore, when the housings 10 and 30 are at the close contact position, the push rods 21 and 41 may be vertically moved integrally. On the other hand, when one of the housings 10 and 30 is rotated by approximately 90° from the close contact position and opened as shown in FIG. 2 (this position will hereinafter be referred to as the open position), the lock between the lock member 8 and the lock groove 21b is released, and it becomes possible to vertically move the push rods 21 and 41 independently of each other.

A protrusion 10a projecting laterally is formed at the upper end section of the first housing 10. When the dual pipette device is grasped by a hand and the push rods 21 and 41 are pushed down, the protrusion 10a contacts the hand to receive a pushing-down force, and facilitates the operation of pushing the push rods 21 and 41 down.

Operations of the dual pipette device constituted as mentioned above will now be described below.

When the dual pipette device is used, the dropping tips 6, for drawing and retaining the sample solution or the reference solution therein are first fitted to the dropping tip fitting sections 12 and 32. Then, the housings 10 and 30 are rotated from the close contact position to the open position around the hinges 2. As a result, as shown in FIG. 3, the distance between the piston members 20 and 40 is increased from d1 at the close contact position to d2 (>d1) at the open position, and it becomes easy to insert only one of the dropping tips 6, into a reagent bottle or the like and to draw the sample solution or the reference solution from the reagent bottle or the like into the dropping tip 6. Also, at the open position, the push rods 21 and 41 are operable independently. Therefore, when the push rod for drawing the sample solution or the reference solution thereinto, for example, the push rod 21, is pushed down to move the piston rod 23 down, the lower end of the dropping tip 6 is dipped in the sample solution or the reference solution in the reagent bottle, and then the push rod 21 is released, the push rod 21 and the piston rod 23 are moved up by the urging force of the upper coil spring 25 and the lower coil spring 26, and the sample solution or the reference solution is drawn into the dropping tip 6. The reference solution or the sample solution is drawn into the other dropping tip 6 in the same manner, and then the housings 10 and 30 are rotated to the close contact position. The distance d1 between the piston rods 20 and 40 with the housings 10 and 30 at the close contact position is adjusted to be equal to the distance between the liquid spotting holes of the slide type ionic activity measuring device. Therefore, when the lower ends of the dropping tips 6, fitted to the dual pipette device are positioned to face the liquid spotting holes and the push rods 21 and 41 are pushed down simultaneously, the sample solution and the reference solution are simultaneously spotted to the liquid /spotting holes. Since the push rods 21 and 41 move only integrally by the lock between the lock member 8 and the lock groove 21b, the push rods 21 and 41 are moved down simultaneously to effect simultaneous spotting of the sample solution and the reference solution when at least one of the push rods 21 and 41 is pushed down.

Of course, when the dual pipette device is used for spotting with the housings 10 and 30 at the open position, it is possible to spot the sample solution and the reference solution independently. Spotting of the sample solution and the reference solution may be conducted independently, for example, in the case where the ionic activity measuring device is provided with multiple pairs of the ion selective electrodes and only the sample solution is to be spotted early since the viscosity of the sample solution is high and the diffusion speed thereof in the liquid distributing member is low.

The aforesaid embodiment should preferably be provided with a lock mechanism, for example, a detent mechanism using a spring or the like, for securing and holding the dual pipette device at the close contact position and the open position, thereby making it possible to secure and hold the housings 10 and 30 at the close contact position and the open position.

Figure 6:
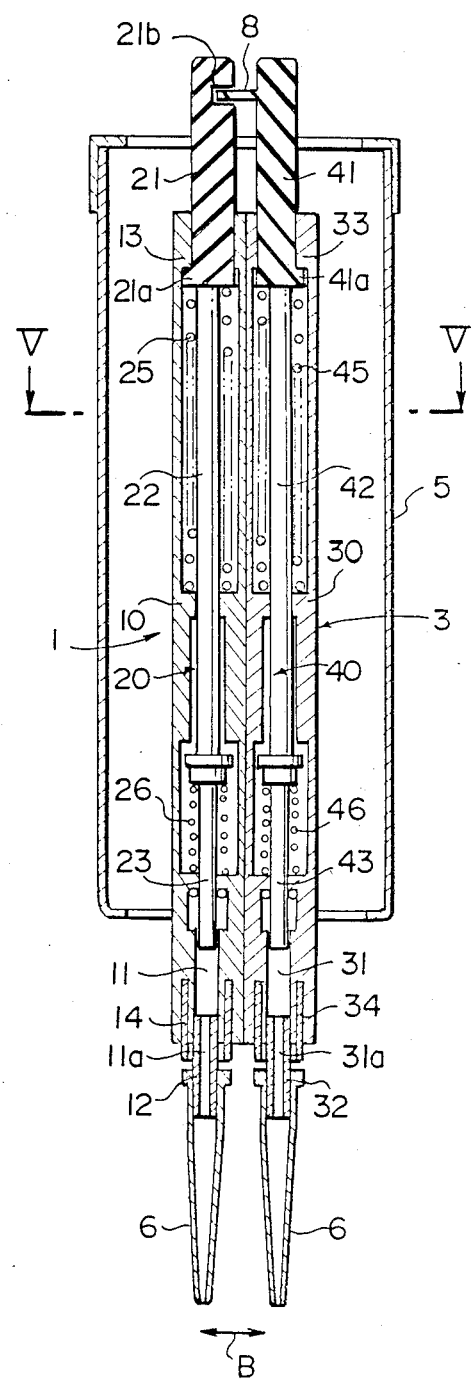
FIG. 6 is a sectional view taken along line A'—A' of FIG. 5, FIGS. 7, 8, 9 and 10 are perspective views showing examples of the mechanism for laterally moving the pipettes in the embodiment of FIG. 5.

FIGS. 5 and 6 show another embodiment of the dual pipette device in accordance with the present invention. In FIGS. 5 and 6, similar elements are numbered with the same reference numerals with respect to FIGS. 1 and 4. This embodiment comprises a holding case 5, and a pair of pipettes 1 and 3 extending vertically in parallel with each other in the holding case and moveable laterally in the direction as indicated by the arrow B. The pipettes 1 and 3 respectively comprise the piston members 20 and 40 vertically extending in the housings 10 and 30, and the cylinders 11 and 31 formed at the lower sections of the housings 10 and 30. In FIG. 5, reference numeral 7 denotes an ejector knob connected to the tip ejectors 14 and 34.

The pipettes 1 and 3 are moveable laterally between the close contact position as shown in FIG. 6 and the open position spaced away from each other as shown in FIG. 5. In order to move the pipettes 1 and 3 laterally with respect to each other, an operating disk 50 mounted on the front surface of the holding case 5 for rotation around a center shaft 53 is rotated. The operating disk 50 is provided with a pair of cam grooves 51 and 52 extending in the spiral form from positions near the center shaft 53 toward the outer circumference of the operating disk 50. Cam shafts 1a and 3a secured to the housings 10 and 30 are engaged respectively with the cam grooves 51 and 52. Therefore, when the operating disk 50 is rotated around the center shaft 53, the cam shafts 1a and 3a are moved laterally along the cam grooves 51 and 52, and the pipettes 1 and 3 are thereby laterally moved in the direction as indicated by the arrow B.

A protrusion 5a projecting laterally is formed at the upper end section of the holding case 5 to act in the same way as the protrusion 10a in the embodiment of FIG. 1.

When the embodiment of the dual pipette device shown in FIG. 5 is used, the dropping tips 6, are fitted to the dropping tip fitting sections 12 and 32, and the operating disk 50 is rotated to move the pipettes 1 and 3 from the close contact position to the open position as shown in FIG. 5, thereby increasing the distance between the dropping tips 6, 6 fitted to the lower ends of the pipettes 1 and 3. After sequentially drawing the sample solution and the reference solution into the dropping tips 6, by operating the push rods 21 and 41 independently in the same manner as the embodiment of FIG. 1, the operating disk 50 is rotated to move the pipettes 1 and 3 to the close contact position, and the sample solution and the reference solution are spotted simultaneously.

The embodiment of FIG. 5 should preferably be provided with a lock mechanism, for example, a detent mechanism using a spring or the like, for securing and holding the pipettes 1 and 3 at the close contact position and the open position.

Figure 8:
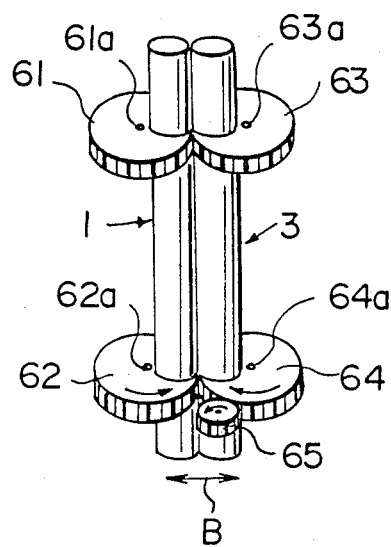
Figure 9:
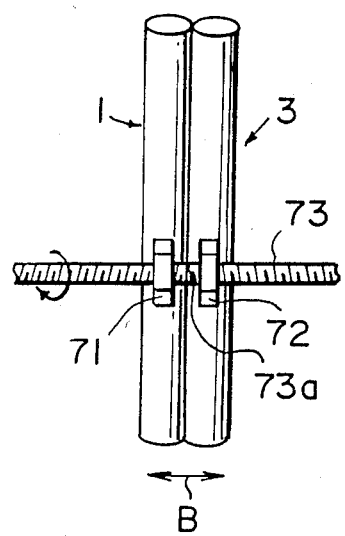
Figure 10:
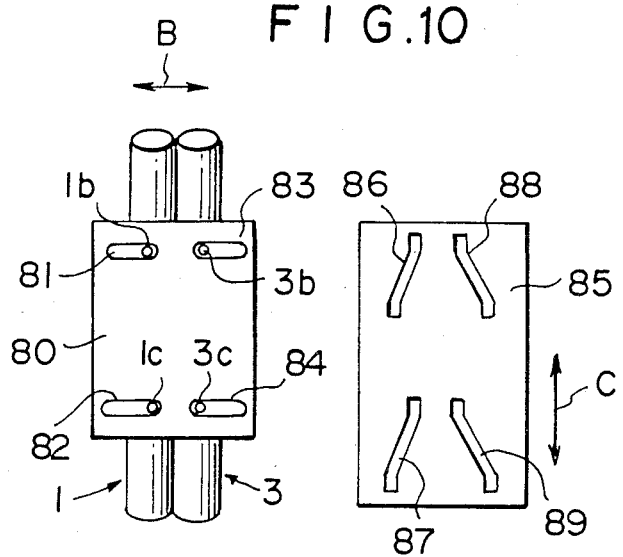

FIGS. 8, 9 and 10 show different examples of the mechanism for laterally moving the pipettes 1 and 3 supported in the holding case 5 for lateral movement.

The mechanism of FIG. 8 comprises upper gears 61 and 63 meshing with each other and respectively having rotation shafts 61a and 63a, and lower gears 62 and 64 meshing with each other and respectively having rotation shafts 62a and 64a. The pipettes 1 and 3 are supported by the gears 61, 62, 63 and 64 at positions eccentric with respect to the rotation shafts 61a, 62a, 63a and 64a as shown, and a drive gear 65 is meshed with the lower gear 64. The drive gear 65 is operated to rotate the gears 61, 62, 63 and 64, thereby laterally moving the pipettes 1 and 3 eccentrically supported by these gears. However, in this case, the lateral movement becomes the movement along circular arcs as the gears 61, 62, 63 and 64 rotate.

The mechanism of FIG. 9 comprises a laterally extending screw member 73 mounted on the holding case 5. Engagement members 71 and 72 meshing with the screw member 73 are secured respectively to the housings 10 and 30. The screw member 73 is rotated to move the engagement members 71 and 72, thereby laterally moving the pipettes 1 and 3. For this purpose, the directions of the threads on the left side and the right side of the center 73a of the screw member 73 are reverse to each other, and the threads of the engagement members 71 and 72 are formed in directions reverse to each other.

In the mechanism of FIG. 10, the pipettes 1 and 3 are laterally moved by using two cam plates 80 and 85. The first cam plate 80 has laterally extending cam grooves 81, 82, 83 and 84, and the second cam plate 85 has upper cam grooves 86 and 88 disposed in the downwardly spreading form, and lower cam grooves 87 and 89 disposed in the downwardly spreading form. The second cam plate 85 is superposed on the first cam plate 80, and cam shafts 1b and 1c secured to the pipette 1 and cam shafts 3b and 3c secured to the pipette 3 are engaged with the cam grooves of the cam plates 80 and 85. The first cam plate 80 allows the pipettes 1 and 3 to move only laterally. Therefore, when the second cam plate 85 is moved up and down in the direction as indicated by the arrow C, the cam shafts 1b, 1c, 3b and 3c are moved laterally respectively along the cam grooves 86, 87, 88 and 89 of the second cam plate 85. As a result, the pipettes 1 and 3 are moved laterally.

FIG. 11 shows a further embodiment of the dual pipette device in accordance with the present invention. In FIG. 11, similar elements are numbered with the same reference numerals with respect to FIG. 5. The embodiment of FIG. 11 has the internal configuration as shown in FIG. 6.

Figure 13:
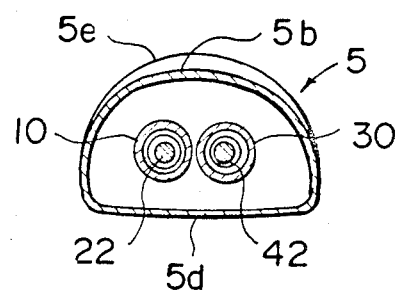
FIG. 13 is a sectional view showing the sectional configuration of the embodiment of FIG. 11 and taken along line B—B of FIG. 11.

In the embodiment of FIG. 11, as shown in FIG. 13, a side surface 5d of the holding case 5 provided with the operating disk 50 is formed flat, and a side surface 5e facing the side surface 5d with the pipettes 1 and 3 intervening therebetween is formed in an approximately cylindrical shape. As shown also in FIG. 11, a finger gripping surface 5b is formed on the approximately cylindrical side surface 5e. The position and the shape of the finger gripping surface 5b are adapted to index, middle, third and little fingers of the right or left hand grasping the holding case 5. The side surface 5e may also be formed in the approximately cylindrical shape by combining several flat surfaces. Since the side surface 5e is formed in the aforesaid shape and provided with the finger gripping surface 5b, the holding case 5 is naturally grasped so that the side surface 5e closely contacts the hand and the side surface 5d remains open. In the case where the holding case 5 is grasped in the reverse direction so that the side surface 5d closely contacts the hand, the pipette operator has an unnatural feeling caused by the sharp corners of the side surface 5d and the finger gripping surface 5b which does not snugly fit to the hand. Also, in this embodiment, the protrusion 5a is formed above the side surface 5e. Therefore, in the case where the holding case 5 is grasped so that the side surface 5d closely contacts the hand, the protrusion 5a contacts near the base portion of the thumb and makes it difficult to grasp the holding case 5. This feature applies to grasping of the holding case 5 by the right hand and grasping thereof by the left hand.

Figure 12:
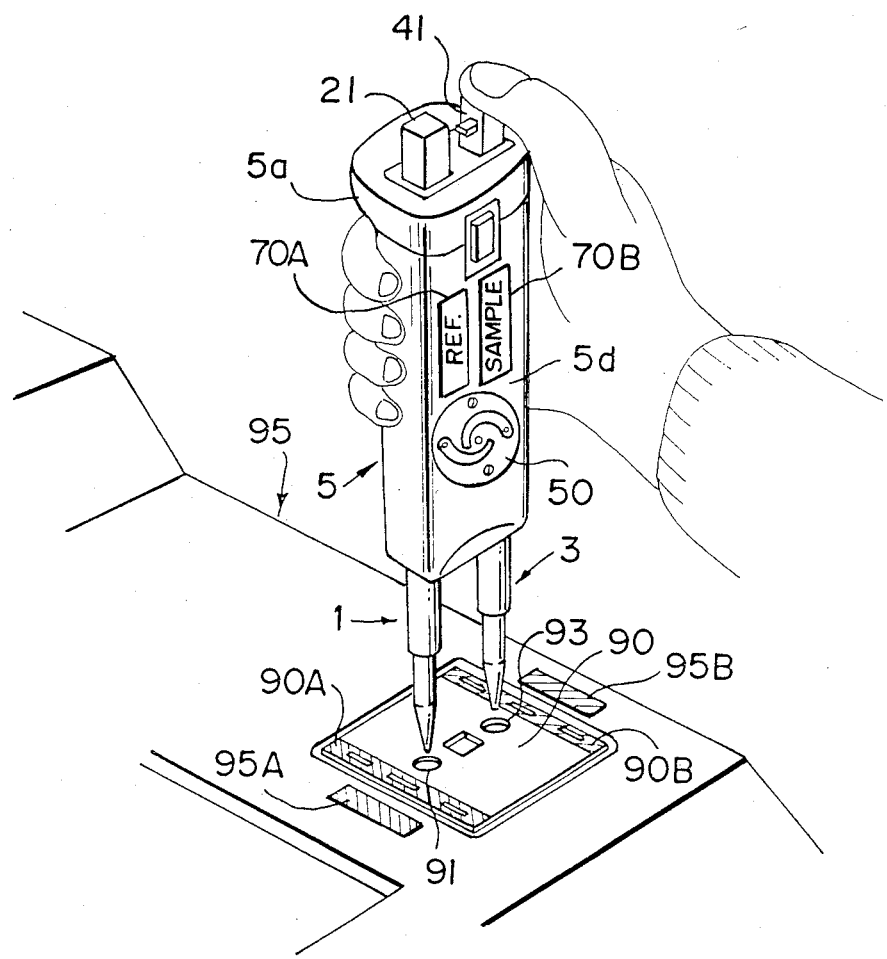
FIG. 12 is a perspective view showing the embodiment of FIG. 11 in the use condition.

As mentioned above, when it is grasped by the right hand and when the holding case 5 is grasped by the left hand, it is grasped always so that the side surface 5e closely contacts the hand. Therefore, as shown in FIG. 12, when the holding case 5 is positioned in front of the operator as usually conducted in the course of pipette operation, the pipette 1 is always positioned on the left side of the pipette operator and the pipette 3 is positioned on the right side thereof. Accordingly, when it is specified by an ionic activity measurement manual or the like that the reference solution be drawn into, for example, the left pipette and the sample solution be drawn into the right pipette regardless of left hand and right hand operations, the reference solution is always drawn into the pipette 1, and the sample solution is always drawn into the pipette 3.

In FIG. 12, reference numeral 90 denotes the slide type ionic activity measuring device, and reference numerals 91 and 93 denote the liquid spotting holes. Also when spotting of the sample solution and the reference solution is conducted as mentioned above, the holding case 5 is grasped in the aforesaid direction. Therefore, when drawing of the reference solution and the sample solution into the pipettes 1 and 3 is conducted as specified above, the reference solution is spotted from the pipette 1 on the left side of the pipette operator, and the sample solution is spotted from the pipette 3 on the right side thereof. Accordingly, when an analyzer 95 for measuring ionic activity by use of the slide type ionic activity measuring device 90 is disposed at a predetermined position with respect to the pipette operator and drawing of the reference solution and the sample solution is conducted as specified above, the predetermined reference solution and the sample solution are always spotted respectively to the liquid spotting holes 91 and 93 of the slide type ionic activity measuring device 90.

However, if setting of the slide type ionic activity measuring device 90 on the analyzer 95 is conducted incorrectly, the sample solution and the reference solution are incorrectly spotted respectively to the liquid spotting holes 91 and 93. As shown in FIG. 12, in order to prevent this problem, color marks 90A and 90B of different colors may be provided at opposite ends of the slide type ionic activity measuring device 90, and a color mark 95A of the same color as the color mark 90A and a color mark 95B of the same color as the color mark 90B may be provided on the section of the analyzer 95 for receiving the slide type ionic activity measuring device 90 at positions adjacent the color marks 90A and 90B. Also, in order to ensure that drawing of the reference solution and the sample solution into the pipettes 1 and 3 be conducted as specified above, color marks of the same colors as the reference solution and the sample solution may be provided on the pipettes 1 and 3, or on the holding case 5 at positions corresponding to the pipettes 1 and 3. In this case, in order to minimize the risk of incorrect spotting, the colors of the color marks should be adjusted to be the same respectively to the colors of the color marks 90A and 90B on the slide type ionic activity measuring device 90, and the colors of the color marks 95A and 95B on the analyzer 95. Instead of the color marks provided on or adjacent the pipettes 1 and 3, character indication sheets 70A and 70B as shown in FIG. 12 may be used.

The mechanism for laterally moving the pipettes 1 and 3 in the holding case 5 is not limited to the mechanism shown in FIG. 11, and any known mechanism may be employed. Also, in order to make the pipettes 1 and 3 operable simultaneously and independently, instead of making the pipettes 1 and 3 moveable laterally and providing the lock member 8 and the lock groove 21b for releasably joining the piston members 20 and 40 together, a mechanism as proposed in Japanese patent application No. 60(1985)-14765 may be employed. In the proposed mechanism, the piston members are provided respectively with an upwardly facing contact section and a downwardly facing contact section. With the dual pipette device wherein the proposed mechanism is employed, when the piston member provided with the downwardly facing contact section is pushed down, the other piston member is moved down together. When the piston member provided with the upwardly facing contact section is pushed down, only said piston member is moved down. The cylinders 11 and 31 need not necessarily be disposed in parallel with each other.

The embodiment of FIG. 11 may also be constituted so that the pipettes 1 and 3 are operable independently. Also in this case, the same effects are obtained when the outer surface of the holding case for holding a pair of the pipettes, or the outer surface of a member for joining the pipettes or a cover member for covering the pipettes (when no holding case is provided) is shaped as mentioned above.

We claim:

1. A dual pipette device comprising:
   (i) a pair of housings joined together by a hinge means at a vertically extending axis, said pair of housings being rotatable with respect to each other about said axis
   (ii) a pair of cylinders, one each disposed respectively at lower sections of each one of said pair of housings,
   (iii) a pair of piston members extending vertically, each one of said piston members being supported by one of said pair of housings or one of said pair of cylinders, and each of said piston members respectively having lower end portions vertically slidable in one of said pair of cylinders, and
   (iv) a pair of dropping tip fitting sections disposed at lower ends of each of said pair of housings or each of said pair of cylinders so that each of said pair of dropping tip fitting sections communicate with one of said pair of cylinders,
   wherein said pair of the piston members are provided with a lock mechanism constructed and arranged for locking said piston members to each other when said pair of housings are rotated and the distance between said pair of piston members becomes not larger than a predetermined distance, so that said piston members are vertically slidable integrally with each other.

2. A dual pipette device as defined in claim 1 wherein each of said piston members comprises: a push rod disposed at an upper end section of said piston member and protruded upwardly from an upper surface of one of said pair of housings, a piston rod disposed at a lower end section of said piston member and fitted to one of said pair of cylinders for vertical sliding in said one of said pair of cylinders, and a connection rod for connecting said push rod to said piston rod.

3. A dual pipette device as defined in claim 1 or 2, further comprising spring means for urging each of said piston members upwwardly.

4. A dual pipette device as defined in claim 2 wherein said lock mechanism comprises a lock groove formed in an inner side surface of one of said push rods and a lock member secured to an inner side surface of the other of said push rods.

5. A dual pipette device as defined in claim 1 further comprising a pair of tip ejectors, one each disposed at a lower end of one of said pair of housings for vertical movement in said housings so as to surround said dropping tip fitting sections, each of said pair of cylinders being provided with a vertical groove inside of which one of said pair of tip ejectors moves.

6. A dual pipette device as defined in claim 5 further conprising ejector knobs provided on outer side surfaces of said housings, and connected to said tip ejectors for ejecting said dropping tip fitting sections.

7. A dual pipette device comprising a holding case, and a pair of pipettes disposed in parallel with each other and vertically extending in said holding case, wherein:
   (i) each one of said pair of pipettes comprises a cylinder, a piston member extending vertically and respectively having a lower end portion vertically slidable in said cylinder, and a dropping tip fitting section disposed at a lower end of said cylinder to communicate with said cylinder.
   (ii) said pair of pipettes are disposed in said holding case so that the distance between said pipettes is changeable, and
   (iii) said pair of piston members are provided with a lock mechanism constructed and arranged for locking said piston members to each other when said pair of pipettes are moved laterally with respect to each other and the distance between said pair of piston members becomes not larger than a predetermined distance, so that said piston members are vertically slidable integrally with each other, and said pair of pipettes being operable separately when in the unlocked state.

8. A dual pipette device as defined in claim 7, wherein each of said piston members comprises a push rod disposed at an upper end section of said piston member and protruded upwardly from an upper surface of said holding case, a piston rod disposed at a lower end section of said piston member and fitted to said cylinder for vertical sliding in said cylinder, and a connection rod located between and connected to said push rod and said piston rod.

9. A dual pipette device as defined in claim 7 or 8 further comprising a pair of coil springs, one of said pair of coil springs urging each of said piston members upwardly.

10. A dual pipette device as defined in claim 7, further comprising a pair of tip ejectors each disposed at a lower end of one of said cylinders for vertical movement in said so as to surround said dropping tip fitting sections, each of said pair of cylinders being provided with a vertical groove inside of which one of said pair of tip ejectors moves.

11. A dual pipette device as defined in claim 10 further comprising ejector knobs provided on an outer side surface of said holding case, and connected to said tip ejectors for ejecting said dropping tip fitting sections.

12. A dual pipette device as defined in claim 8 wherein said lock mechanism comprises a lock groove formed in an inner side surface of one of said push rods and a lock member secured to an inner side surface of the other of said push rods.

13. A dual pipette device as defined in claim 7, further comprising operating disk means provided with a pair of cam grooves extending in a spiral form from positions near the center of said operating disk means towards the outer circumference thereof and engaging with cam shafts secured to each of said pipettes said operating disk means cooperating with said cam shafts to move said pipettes laterally upon rotation of said operating disk means.

14. A dual pipette device as defined in claim 7, further comprising eccentric gear means to which said pipettes are secured, said gear means moving said pipettes laterally upon rotation of said gear means.

15. A dual pipette device as defined in claim 7, further comprising screw means meshed with engagement members respectively secured to housings of said pipettes, said screw means cooperating with said engagement members to move said pipettes laterally upon rotation of said screw means.

16. A dual pipette device as defined in claim 7, further comprising means for relatively laterally moving said pipettes, comprising; a first cam plate provided with laterally extending cam grooves, and a second cam plate superposed on said first cam plate and provided with cam grooves disposed in a downwardly spreading form, said cam grooves of said first cam plate and said second cam plate being engaged with cam shafts secured to said pipettes.

17. A dual pipette device as defined in claim 7 wherein one side of the outer surface of said holding case includes a hand grasping portion shaped and sized such that said holding case may be positioned in close contact with fingers of a user's hand, and wherein the other side of the outer surface of said holding case is approximately cylindrical in shape.

18. A dual pipette device as defined in claim 7, wherein said pair of pipettes are disposed in parallel with each other inside of a holding case, wherein one side of the outer surface of said holding case includes a hand grasping portion shaped and sized such that said outer surface may be positioned in close contact with the fingers of a user's hand, and wherein the side opposite said one side is shaped so that said hand grasping said holding case will not be in close contact with said opposite side.

* * * * *